United States Patent [19]

Maurer et al.

[11] 4,180,473
[45] * Dec. 25, 1979

[54] METHOD OF TRANSPORTING METAL IONS

[75] Inventors: Gerald L. Maurer, Fairfield; Sudhir K. Shringarpurey, Avon Lake, both of Ohio

[73] Assignee: National Research Laboratories, Cincinnati, Ohio

[*] Notice: The portion of the term of this patent subsequent to Oct. 25, 1994, has been disclaimed.

[21] Appl. No.: 844,280

[22] Filed: Oct. 21, 1977

Related U.S. Application Data

[63] Continuation-in-part of Ser. No. 719,813, Sep. 1, 1976, Pat. No. 4,129,509, which is a continuation-in-part of Ser. No. 597,756, Jul. 21, 1975, Pat. No. 4,055,655.

[51] Int. Cl.$^2$ .......................... C09K 3/00; C02B 5/06
[52] U.S. Cl. ................................... 252/182; 252/49.5; 252/180; 252/312; 252/356; 252/DIG. 11; 424/287; 424/289; 424/290; 424/291; 424/294; 424/295; 424/DIG. 6
[58] Field of Search ............... 252/356, 180, DIG. 11, 252/182

[56] References Cited

U.S. PATENT DOCUMENTS

| | | | |
|---|---|---|---|
| 3,240,701 | 3/1966 | Furia | 252/49.5 X |
| 3,365,397 | 1/1968 | Kolarik | 252/49.5 X |
| 3,905,909 | 9/1975 | Bauer | 252/156 |
| 4,055,655 | 10/1977 | Maurer et al. | 424/294 |

OTHER PUBLICATIONS

Chemical Abstracts, vol. 75, No. 5, Aug. 2, 1971, p. 164, Avakyan, Z. et al., "Comparative Toxicity of Free Ions and Copper Complexes with Organic Acids for Candida Utilis."
Bobtelsky, M. et al., "The Metallic Complexes of Tartrates and Citrates...", in J. Amer. Chem. Soc., vol. 67, pp. 1824–1831, Oct. 1945.

Primary Examiner—Richard D. Loevering
Attorney, Agent, or Firm—Wood, Herron & Evans

[57] ABSTRACT

A method of transporting metal ions by introducing a metal complex into a medium containing a moiety which demands the metal ion and the complex releases the ions in a controlled manner upon demand. The metal complexes have an aqueous proton induced dissociation property represented by a sigmoidally-shaped curve on a cartesian coordinate plot of the negative log of the metal ion concentration versus the negative log of hydrogen ion concentration. This dissociation property causes a controlled release of metal ion into mediums containing a reacting moiety upon demand for the metal ion. For example, metalworking emulsions of oil and water are stabilized by the addition thereto of minor amounts of a metal complex, e.g., disodium monocopper(II) citrate, which at alkaline pH metalworking conditions above about 7 to about 9 releases metal cations to the emulsions imparting stabilizing characteristics which prevent emulsion degradation by a number of factors commonly encountered in metalworking operations. Also, the method is effective in the controlled release of metal ions in the normal range of physiological pH, i.e., about 4 to 9, for growth controlling action against microorganisms including bacteria, fungi and viruses.

15 Claims, 1 Drawing Figure

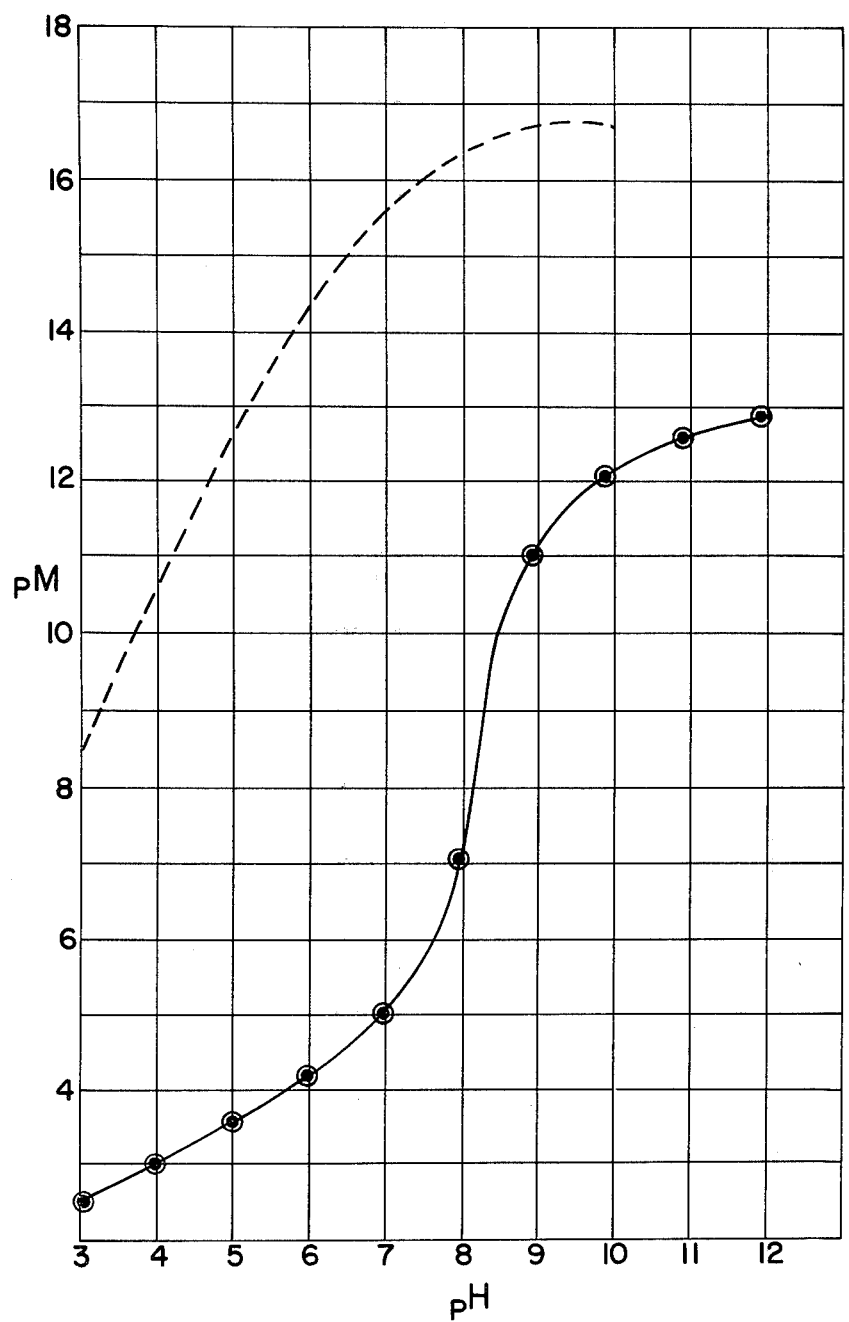

METHOD OF TRANSPORTING METAL IONS

RELATED APPLICATIONS

This application is a continuation-in-part of application Ser. No. 597,756 filed July 21, 1975, (now U.S. Pat. No. 4,055,655) and also a continuation-in-part of application Ser. No. 719,813 filed Sept. 1, 1976, and now U.S. Pat. No. 4,129,509, which itself is a continuation-in-part of Ser. No. 597,756, (now U.S. Pat. No. 4,055,655) each by Sudhir K. Shringarpurey and Gerald L. Maurer.

BACKGROUND OF THE INVENTION

Methods of delivering metal ions in reaction media for co-action with moieties to achieve specific effects are well established.

For instance, a number of inorganic substances have antimicrobial activity because of the toxicity to microorganisms of the ions into which they dissociate. It has been established in antimicrobial activities that salts of heavy metals are rapidly precipitated by extraneous organic or other material and, therefore, while such salts may have an initial cell kill at an initial effective concentration, the effective concentration is rather quickly reduced by combination of the metal with such extraneous matter, thereby depleting the amount of toxic metal available for biocidal activity. Therefore, while inorganic salts offer in certain instances the property of aqueous solubility and, therefore, dissociation for availability as toxic metal agents, they may be rendered rather quickly ineffective such that prolonged or controlled destruction or inhibition of bacterial action is unavailable. On the other hand, metal salts or complexes of organic moieties such as organic acids or the like possess a degree of dissociation which is normally not as great in comparison to, for example, highly soluble inorganic salts. Therefore, whereas the metal organic salts or metal complexes may have a greater stability or kinetic inertness with respect to extraneous organic matter present in the environment of living cells, there is also generally a loss of toxic effect by reason of their higher stability. Representative of prior art patents directed to the use of metal salts or metal chelates of inorganic or organic compounds as microbiocidal agents are: U.S. Pat. Nos. 871,392; 991,261; 1,679,919; 1,785,472; 2,208,253; 2,269,891; 2,456,727; 2,494,941; 2,878,155; 2,900,303; 2,091,393; 2,938,828; 3,076,834; 3,099,521; 3,206,398; 3,240,701; 3,262,846; 3,266,913; 3,681,492 and 3,782,471.

In other instances, various prior art approaches have been taken toward the improvement of metalworking compositions and in an effort to overcome or minimize direct and indirect disadvantages involved in the use of such metalworking fluids. Representative of prior art patents in this area are U.S. Pat. Nos. 2,688,146; 3,240,701, 3,244,630 and 3,365,397. Such patents and the efforts of others in substance have been directed to overcoming the factors contributing to emulsion deterioration and breakdown by the addition of metal compounds and complexes.

In substance, in such prior art processes there appear to have been two extremes made available. On the one hand, known metal compounds have a high degree of dissociation such that metal ions are quickly and copiously made available by virtue of rapid dissociation with formation of ionized species. These species react so as to saturate all available reacting moieties; and thereby are rendered inactivated in a very narrow time frame, thus rendering them relatively ineffective as biocidal agents, or metalworking stabilizers and the like, over prolonged periods of time. Other known metal compounds are relatively stable and provide minimal amounts of ionized species with minimal effects.

SUMMARY OF THE INVENTION

As disclosed in our earlier applications above mentioned, the antimicrobial activity of certain metal complexes, e.g., the dialkali monocopper(II) citrates, has been established by their toxic and growth-inhibiting action against a number of microbes. These metal complexes have also been found to have a very unexpected dissociation property in about the normal range of physiological pH. The dissociation property is represented by a sigmoidally shaped curve, i.e., one curved in two difference directions, like the letter "S", on a cartesian coordinate plot of the negative log of metal ion concentration versus the negative log of hydrogen ion concentration (or otherwise known as a pM-pH diagram). This unique dissociation property of the metal complexes thereby renders them extremely effective in the controlled release of toxic metal ion from the complex at a pH compatible with growth of bacteria. Also, metalworking emulsions, i.e., oil and water dispersions, are stabilized by the addition of an effective stabilizing amount of a metal complex of a metal ion and a polyfunctional organic ligand. The aqueous proton induced dissociation property causes the controlled release of metal ion into the oil and water dispersions to impart metalworking stability to the dispersions. Quite unexpectedly, it has been discovered that metalworking fluids can be stabilized against attack and deterioration by different causes. Thus, metalworking stability is not only achieved against bacteria, but the fluids are stabilized against degradation by physical, chemical, and physicochemical causes associated with metalworking conditions including heat, pressure, metalworking compositional environment of metalworking particles, polyvalent ions, etc. Metal complexes are also provided which have stability at high alkaline pH's on the order of about 8 to about 12 and, therefore, such complexes are very advantageously employed in alkaline media providing controlled release, upon demand, of their antimicrobial or other activities. This has been fully developed in our copending applications which are embodied herein for further details.

This application is directed to another aspect of our discoveries, namely, a method for transporting metal ions in controlled amounts in a medium containing a moiety demanding said metal ions. This broader concept is embodied, by way of example, in our earlier disclosures of antimicrobial and metalworking stabilizer activities discussed above. The method comprises the introduction of an effective amount of a metal complex of a metal ion and a polyfunctional organic ligand. The complex has an aqueous proton induced dissociation property represented by a sigmoidally-shaped curve on a cartesian coordinate plot of the negative log of the metal ion concentration versus the negative log of the hydrogen ion concentration. The dissociation property of the complex provides the controlled release of metal ions upon demand of the moiety. Further, the dissociation is regulated by control of pH.

In the cases of the metalworking and microbial environments, the controlled release and demand are propagated by bacteria, metalworking particles, polyvalent metal ions, etc., and other moieties demanding the metal ion. Thus, antimicrobial and metalworking stabilizing activities are achieved by such release. However, these environments illustrate specific moieties and it will be appreciated that other moieties can be satisfied and stabilized or interacted with to achieve other useful results by the method of this invention.

Thus, this invention fulfills a need in other areas where transport of metal ions is required in controlled amounts upon demand. This is particularly illustrated by antimicrobial activities where toxic metal ions are required in large amounts in the normal range of physiological pH, i.e., about 4 to about 9. In particular, the method of this invention provides release of large amounts of toxic metal ion from the metal complexes at a pH between about 7 and 9, because of their relative instability at about pH 7 where almost all microorganisms are viable. These complexes are very stable and relatively inert to organic moieties, unlike multivalent soluble salts of the prior art which usually are caused to precipitate. Such agents are extremely stable even at high alkaline pH's. Yet, upon demand, by reason of their unique dissociation property as demonstrated by sigmoidally shaped behavior on a pM-pH diagram, these agents offer controlled release of metal ions at a pH where nearly all bacteria are believed to grow. Such method of transport employing a complex which dissociates upon demand at the pH most amenable to the activity of the moiety being acted upon, for example bacteria, is a unique general method.

The metal transport method of this invention is thus to be differentiated from methods which employ other complexing agents. For example, the complexes of this invention are to be differentiated from other metal complexes wherein metal cations have been complexed with organic ligands represented by ethylenediaminetetraacetic acid (EDTA), diethylenetriaminepentaacetic acid (DTPA), other amino acids, or the like which have relatively high stability or chemical inertness and which do not offer a controlled release of toxic metal ion or dissociation property represented by a sigmoidal pM-pH diagram. Rather, known metal complexes by reason of their stability and chemical inertness will tend to dissociate to a lesser extent in rather linear fashion over the normal physiological pH range. Furthermore, this invention provides an antimicrobial metal complex which is capable of aqueous solubility in high concentration by reason of its ionic character and yet remains in a stable form. This property of solubility in water or in neutral, acid or alkaline media enables the production of concentrates capable of producing upon demand toxic metal ion in a range of pH environment from 3 to 12, and the physiological range of 4 to 9. Such a solubility property is to be distinguished from the rather insoluble metal compounds of the prior art which employ metal cation-anionic components and which are virtually insoluble in aqueous media; or those metal complexes which, even though they are soluble, bind the metal ion in such a complexed state that it is only slightly dissociated and, therefore, scarcely available for action. Also, metal complexes employed in the methods of this invention release large amounts of metal ion from their coordinate structures at a pH of about 4 to about 9 and, most preferably at a pH of between about 7 and about 9 or 10, i.e., those which are normally encountered in many useful working conditions. Upon demand, by reason of their unique dissociation property as demonstrated by sigmoidally shaped behavior on a pM-pH diagram, these agents offer controlled release of metal ions at a pH compatible with metalworking, antimicrobial, and other utilitarian conditions.

DETAILED DESCRIPTION OF INVENTION

The following detailed description is with reference to the employment of the metal transport agent in metalworking and antimicrobial environments, as examples, where the metal ion is transported in a medium containing a moiety demanding the metal ion and the metal ion is released in a controlled manner upon demand.

In a presently preferred form, the transport agent of this invention comprises a monometal complex of a multivalent metal and a polyfunctional organic ligand in a ratio of 1:1 of the metal to the ligand, the complex having a dissociation property represented by a sigmoidally shaped plot on a pM-pH diagram A specific example of the metal complex is dialkali metal monocopper (II) citrate represented by disodium-, dipotassium- or dilithium- monocopper(II) citrate. These dialkali monocopper(II) citrates have a dissociation property represented by a sigmoidal plot wherein the curve of two directions meets at a point within the pH range of about 7 to about 9. It has been established that these monocopper(II) complexes in basic media, on the order of about pH 9 to about 12, are very stable, i.e., have an effective stability constant, $K_{eff}$, on the order of about $10^{12}$ to about $10^{13}$. However, $K_{eff}$ of these monocopper(II) citrate complexes at a pH of about 7-8 are on the order of about $10^5$ to about $10^8$. Therefore, at or about a pH around 7-8, the effective stability constant of the monocopper(II) citrate complex is considerably lower (a thousand to several hundreds of thousand times lower) and a significant free $Cu^{++}$ concentration is available for toxic or stabilizing activity. For example, about 10% of the copper in the complex is in the ionized state at or about pH 7 while approximately 0.1% of the copper is ionized at or about pH 9. This would not be true for an EDTA or polyamine complex of a multivalent metal such as copper, since its stability constant ($10^{14}$ to $10^{16}$) will vary only slightly in the normal pH of 7 to 9. Such EDTA complexes do exhibit a pH effect on the stability constant, but it is represented by a smooth, monotonic curve reaching a limiting effect by proton induced dissociation at pH values from about 7 to about 9, yielding only from about 0.001% ionized species at or about pH 7 to as little as 0.00001% ionized species at or about pH 9. It is to be understood that the stabilizing or antimicrobial complexes will operate over a pH range of about 3 to about 12. Above about pH 12, the complexes tend to be destroyed by the alkaline media, precipitating from the media as hydrous metal oxides. Below about pH 6, i.e., about 3 to about 6, the instability of the metal complex results in a high concentration of the free $Cu^{++}$ in solution which will effect biostability and other stabilizing functions as above mentioned. In the mid range of about 7 to about 9, the controlled release is most effective. Thus, these complexes provide controlled release of metal ion between about 10% to about 0.1% of a complexed metal in the pH range of about 7 to 9, which metal ion is then available for coordination, antimicrobial and stabilizing functions.

In accordance with this description and the presently preferred embodiment, it will become apparent that other metal complexes of polyfunctional organic ligands respond to the model of this invention where they exhibit the dissociation property characterized by a sigmoidal curve on a standard pM-pH diagram. For example, based upon the monometal-polyfunctional organic ligand complex of this invention, other metal ions of a monovalent or multivalent nature, specifically divalent and polyvalent cations including zinc, nickel, chromium, bismuth, mercury, silver, cobalt, and other similar metallic or heavy metal cations may be employed. The complexes of heavier metals are considered more toxic than those of the lighter metals. Other polyfunctional organic ligands may be substituted for the citric acid specifically exemplified by the preferred embodiment of this invention. Included among other polyfunctional ligands are the broader class of alpha or beta hydroxy polycarboxylic acids into which class the citric acid falls. Also, other functionally substituted acids such as alpha or beta amino, sulfhydro, phosphinol, etc., can be substituted in the molecular model of the metal complexes of this invention and similar results can be achieved. In general from a metal complex formula standpoint, the monometal complex of copper and citric acid corresponds to a complex formula exhibited by either of the following structural forms (A) and (B).

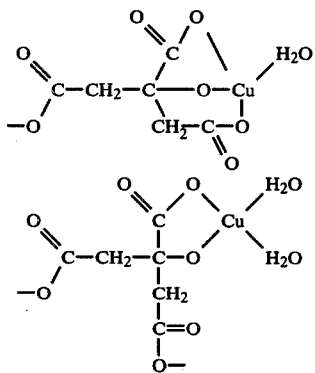

The (A) form is believed to be the preferred form by applying free energy considerations. A single proton introduced into the complex structure represented by either form (A) or (B) prevents the formation of stable 5- or 6- member coordinate rings. With the introduction of a proton, only 7- member rings may be formed by the coordination of the acetate electron donors and such 7-member ring structures are unstable. Therefore, the complex molecule dissociates and presents the metal ion for its toxic or stabilizing effects. In comparison, metal complexes of EDTA or other polyamines require four or more protons, and hence greater acidity, to dissociate the complex; this accounts for the small pH effect exhibited by such complexes in a pM-pH diagram.

The (A) and (B) structural forms may be more generally represented by the following models:

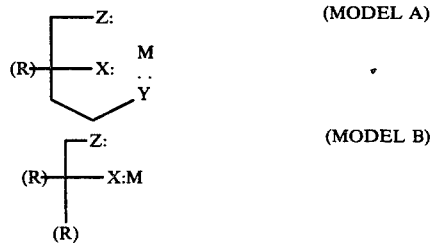

In the above models, the solid line segments represent a chemical bond between elements in the skeletal structure of the molecule; X, Y and Z represent electron pair donors; (R) represents any elemental or molecular species or group; M represents a metal and wherein the proton affinity of X is greater than that of Z, Y or R. It will therefore be appreciated that other Lewis base proton pairs, and other metal ions, may be substituted into these structural models for oxygen, divalent copper, or, for that matter, the carbon atoms to provide a molecular model which will similarly dissociate upon the introduction of one proton or similarly behaving species as exhibited by the sigmoidal behavior on a pM-pH diagram. The molecular models are thus alternative expressions for the complexes of this invention.

The invention and its various embodiments and advantages will be further understood with reference to the following examples, detailed descriptions and the drawing which illustrate the preparation of the complexes, and their activity.

I. PREPARATION OF COMPLEXES

A. Dilithium monocopper(II) citrate 10 millimoles of lithium citrate were dissolved in 10 milliliters of water. To this solution, 10 millimoles of cupric chloride ($CuCl_2 \cdot 2H_2O$) were added gradually with stirring. A deep blue solution was formed. This was neutralized to a pH of about 7 with 10 millimoles of lithium hydroxide ($LiOH \cdot H_2O$). This solution, when evaporated to dryness, gave a deep blue, semicrystalline solid. This solid was ground to a fine powder and the lithium chloride was extracted with 50 milliliters of dry methanol, five times, at 35° C. The blue solid which remained behind was evacuated to remove methanol and desiccated. An attempt was made to crystallize the salt from water-organic solvent systems, but apparently due to the extremely hygroscopic nature of the salt and the high negative charge on the ionized molecule, the solid obtained was microcrystalline to amorphous. The following formula is proposed for the 1:1 complex of copper and citrate based on elucidation of the structure and analyses described hereinafter.

$$Li_2CuC_6H_4O_7 \cdot XH_2O$$

Depending upon the degree of hydration, the following formula weights (F.W.) and corresponding percentages of copper content are proposed:

$Li_2CuC_6H_4O_7 \cdot XH_2O$

| F.W.: | 265.51 for X = 0, | % Cu = 23.93 |
|---|---|---|
| F.W.: | 283.53 for X = 1, | % Cu = 22.41 |
| F.W.: | 301.54 for X = 2, | % Cu = 21.07 |
| F.W.: | 319.56 for X = 3, | % Cu = 19.88 |

The observed copper content of variously dried samples of the solid complex ranged from 20% to 23%. The compound (1:1 solid complex) was extremely soluble in water. A solution as strong as two molar could be made quite easily. Up to a pH of 11.5, there was no effect on the solubility of the compound in water. Beyond this pH, the complex decomposed to a greenish-brown precipitate, probably hydrous copper oxides. The 1:1 solid complex may be used as a stabilizing agent with or without the removal of lithium chloride formed during its preparation.

B. Disodium monocopper(II) citrate (1) Equimolar solutions of copper chloride and sodium citrate were added to water as in A above to obtain a deep blue solution having a pH of about 5. A 50 ml. aliquot of this solution was placed in a separatory funnel. An equal volume of anhydrous acetone was added and the funnel was shaken so as to effect mixing. Upon standing, a two-phase system existed. A blue liquid phase rested on the bottom of the funnel in a reduced volume of approximately 25 ml., while the top layer (approximately 75 ml.) was slightly hazy and colorless, having been crystal clear prior to the shaking process. The blue liquid (oily, viscous) was removed from the funnel through the stopcock and collected in a second separatory funnel. The hazy supernatant was placed in a beaker and evaporated to dryness over a steam bath. An approximate 25 ml. aliquot of anhydrous acetone was added to the second separatory funnel, causing almost instantaneous formation of a plastic-like mass in the bottom of the funnel, as opposed to the oily liquid which had been present there. The supernatant from the plastic mass was placed in a second beaker and labeled supernatant 2. The addition of distilled water to the plastic-like mass resulted in the immediate re-solution of the material. The total volume of the redissolved substance was adjusted to 25 ml., resulting in the formation, once again, of a viscous, oily liquid. Following evaporation to dryness of supernatant 1, microscopic examination of the dry residue revealed the presence of definite, copious amounts of sodium chloride crystals. Evaporation of supernatant 2 yielded a very finely divided powdery residue, containing a small number of distinct sodium chloride crystals. Analysis of the twice-extracted blue oily solution for copper content revealed that the solution contained approximately 125 mg. of copper per milliliter, thereby representing a concentrate of the metal complex which had originally contained approximately 65 mg. per milliliter. The large reduction of the amount of sodium chloride in supernatant 2 indicated that the bulk of the contaminating by-product salt had been removed. A portion of the concentrate was permitted to evaporate and definitive crystalline material was noted.

(2) The procedures of the preceding paragraph (1) were repeated except that there was a pH adjustment of the initially formed blue solution from about pH 5 to about pH 7 with KOH solution to neutralize the HCl formed. After extraction and evaporation procedures were performed as above, a concentrate of the metal complex was obtained which upon evaporation yielded definite crystalline material.

(3) Equimolar aliquots of copper sulfate and sodium citrate as in paragraph (1) were combined followed by pH adjustment of about 7 with NaOH. Procedures of extraction and evaporation of the resulting blue solution as described above yielded an amorphous powder possessing no visually discernible crystalline structure.

The following formula is proposed for the disodium monocopper(II) citrate prepared in paragraphs (1) to (3) above based on the elucidation of the structure and analyses described hereinafter:

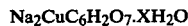

$Na_2CuC_6H_2O_7 \cdot XH_2O$

C. Disodium monozinc citrate

Employing the following ingredients, a zinc complex stabilizer analogous to the copper complex of B above was prepared:

| | |
|---|---|
| 50 ml. | cold water |
| 29.4 g. | trisodium citrate dihydrate |
| 13.6 g. | zinc chloride ($ZnCl_2$) |
| concentrated HCl | |
| NaOH pellets | |

The $ZnCl_2$ was ground into fine particles using a mortar and pestle and then dissolved in the water. The pH was adjusted to between 0.5 and 1.0 with HCl. The sodium citrate was added slowly, with addition of HCl to maintain the pH below 1.0. When all material was dissolved, the solution was neutralized slowly with NaOH pellets. The material remaining in solution at pH 7.2 was decanted, adjusted to a pH of 8.5–9.0 and then extracted with a double volume of a 50:50 methanol acetone solution. The material was collected on a Buchner funnel using Whatman #42 filter paper. Alternatively, the solution can be vacuum dried at 70° C.

D. Disodium mononickel citrate

A nickel complex stabilizer was prepared employing the following ingredients:

| | |
|---|---|
| 40 ml. | cold water |
| 38.4 g. | anhydrous citric acid |
| 47.5 g. | nickel chloride ($NiCl_2$), finely ground |
| NaOH flakes | |

The citric acid was dissolved in the water. The nickel salt was added slowly, with constant monitoring of the pH. When all of the material was in solution, NaOH flakes were added slowly (to minimize heat generation) to adjust the pH to between 4.0 and 5.0. The yield was about 100 ml containing about 117 mg/ml $Ni^{++}$.

II. DETERMINATION OF METAL COMPLEX DISSOCIATION

The dissociation property of the 1:1 copper citrate complex prepared by the above techniques was determined over a pH range of 3–12 units using a copper(II) ion specific electrode ([Orion CopperII] Specific Electrode). 50 milliliter samples of copper citrate 1:1 solution (0.0068 molar) were adjusted to pH 3, 4, 5, 6, 7, 8, 9, 10, 11 and 12, with the concentration of free copper ion subsequently determined by using the copper ion specific electrode. The following values of free copper ion concentrations at the indicated pH were obtained and the negative logs of the copper ion concentration determined.

TABLE

| pH | $Cu^{++}$ | pM |
|---|---|---|
| 3 | $3.2 \times 10^{-3}$ | 2.495 |
| 4 | $9.0 \times 10^{-4}$ | 3.046 |
| 5 | $2.5 \times 10^{-4}$ | 3.602 |
| 6 | $5.3 \times 10^{-5}$ | 4.276 |
| 7 | $1.0 \times 10^{-5}$ | 5.000 |
| 8 | $8.0 \times 10^{-8}$ | 7.097 |
| 9 | $8.8 \times 10^{-12}$ | 11.055 |
| 10 | $9.6 \times 10^{-13}$ | 12.018 |
| 11 | $3.3 \times 10^{-13}$ | 12.482 |
| 12 | $1.34 \times 10^{-13}$ | 12.873 |

From these data, a pM-pH curve was constructed to indicate the relationship between free $Cu^{++}$ ion concentration and pH as illustrated in the drawing. The drawing is a cartesian coordinate plot (solid black line) of the negative log of the metal ion concentration (pM) versus the negative log of the hydrogen ion concentration (pH) at points listed in the above TABLE. This plot is a sigmoidally shaped curve representative of the proton induced dissociation property of the metal complex. At the pH range of about 9-12, the complex is very stable and the free $Cu^{++}$ concentration is low. At a pH of about 7, the complex is relatively unstable and dissociation into free $Cu^{++}$ is significant, enabling stabilizing function. In the range of between about 7 to about 9 the $Cu^{++}$ is available for controlled release; from about 10% to about 0.1% dissociation of $Cu^{++}$ from the complex occurs. This unexpected dissociation versus pH behavior renders the complexes extremely effective as antimicrobial or stabilizing agents for metalworking compositions.

In comparison, a Cu EDTA complex curve is represented by the broken line in the drawing as reported by A. Ringbom, "Complexation in Analytical Chemistry", J. Wiley & Sons, N.Y., 1963, p. 360. As illustrated, the pH effect on Cu EDTA complex is represented by a smooth, monotonic curve reaching a limiting effect by proton induced dissociation at about pH 7-9, thereby yielding, for example, only from about 0.001%–0.00001% ionized species.

Complexes of the ratio one metal:one citrate may have been suggested to exist in dilute solutions in the publication of M. Bobtelsky and J. Jordan, *J. Amer. Chem. Soc.*, Vol. 67 (1945), p. 1824. However, no one has reported the remarkable antimicrobial or emulsion stabilizing activities of these derivatives or their abilities to form coordinate structures with emulsified droplets. Moreover, we have also discovered even further unique attributes of such complexes in metalworking fluids. In addition, such utilities are representative of the metal transport method of this invention.

Further, we have prepared solid metal complexes of the dialkali monocopper(II) citrates and such solid forms are surprisingly unexpected. We have also been able to make high solution concentrations of such metal complexes. The nature of these complexes has definitely been established by using analytical criteria, namely: (1) the mole ratio method introduced by Yoe and Jones (Yoe, J. H. & Jones, A. L.: *Ind. Eng. Chem. Anal.* Edition, 16; 111, 1944); (2) the method of continuous variation attributed to Job and modified by Vosburgh and Cooper (Vosburgh, W. C. & Cooper, G. R.: *J. Am. Chem. Soc.*, 63; 437, 1941); (3) dependence of complex formation on pH and (4) determination of the apparent stability constant of the complex. Spectrophotometric studies, including visible and ultraviolet spectroscopy, pH determinations, as well as infrared spectroscopic measurements were utilized as an additional means of confirmation of our findings on the formation and molecular composition of the 1:1 copper(II) citrate complex.

The 1:1 copper complexes employed here as antimicrobial or stabilizing agents are highly soluble indicating that such complexes are ionic in nature. This is further supported by the observation that the color band of solution of the complex migrated toward the anode (positive electrode) in electrophoresis experiments. Visible and UV spectra exhibit 1:1 compound formation. The overall reaction for the complex formation of the (B) structural form appears to be:

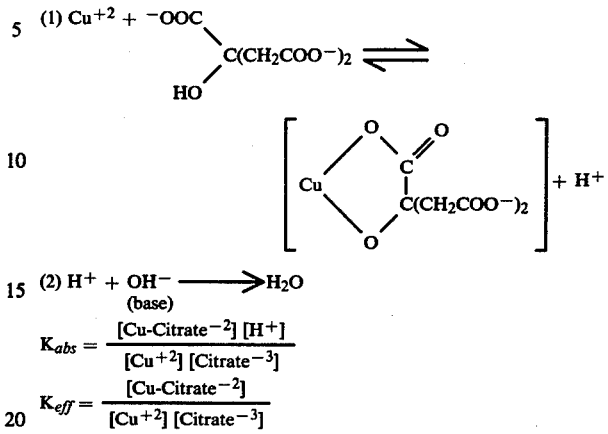

$$K_{abs} = \frac{[\text{Cu-Citrate}^{-2}][H^+]}{[Cu^{+2}][\text{Citrate}^{-3}]}$$

$$K_{eff} = \frac{[\text{Cu-Citrate}^{-2}]}{[Cu^{+2}][\text{Citrate}^{-3}]}$$

Thus, instead of complexing the $-COO^-$ groups only, the alcohol, $-OH$, ionizes and is involved in the coordination. This forms a stable 5-member and probably 6-member ring. Thus, the reaction is drawn to the right (stabilized) by $OH^-$ (base) as the product $H^+$ is then removed as the reaction proceeds. This results in the very high effective stability constant, $K_{eff}$. The $K_{eff}$ for such a reaction is pH dependent but related to the absolute stability constant, $K_{abs}$ by the relationship.

$$K_{eff} = \frac{[\text{CuCitrate}^=]}{[Cu^{++}][\text{Citrate}^{-3}]}$$

$$K_{abs} = \frac{[\text{CuCitrate}^=][H^+]}{[Cu^{++}][\text{Citrate}^{-3}]}$$

$$K_{abs} = K_{eff} \cdot [H^+]$$

We have found that $K_{abs}$ for the 1:1 complex has a constant value of about $10^{13}$ (a strong complex) over a pH range of about 9-12. The apparent value of $K_{abs}$ drops sharply at pH 7 to 9 and, at pH values less than about 7, there is a further decrease indicating that the complex exists in finite concentrations even at pH 3 to 7.

III. ANTIMICROBIAL ACTIVITY

The following experiments were performed to illustrate the biocidal efficacy of the disodium monocopper(II) citrate of this invention versus the prior art dicupric(II) citrate. The following materials, apparatus and procedures were employed.

MATERIALS

1. Three representative test organisms were chosen for the test:
   a. Staphylococcus aureus, designated "SA", ATCC#12600
   b. Aerobacter aerogenes, designated "AA", ATCC#13048
   c. Pseudomonas aeruginosa, designated "PA", ATCC#10145

"ATCC#" is the American Type Culture Collection#.

2. Trypticase soy broth, Difco, prepared in the specified manner by dissolving in hot water and autoclaving, capable of supporting favorable growth in the test organisms.

3. MacLaglan Turbidity Standards for estimation of bacterial growth in broth.

4. Millipore bacterial filter system for estimation of bacterial viability and quantitation of viable organisms.

5. Disodium monocopper(II) citrate, $Na_2CuC_6H_4O_7 \cdot xH_2O$, molecular weight, 297, solid, prepared as above, designated "MCC".

6. Dicupric(II) citrate, $Cu_2C_6H_4O_7 \cdot 2\frac{1}{2}H_2O$, molecular weight, 360, solid, prepared according to National Formulary specifications, designated "DCC".

7. Coleman Jr. Spectrophotometer for quantitation of turbidity, where "OD" is measure of optical density and "OS" means the instrument went off scale due to turbidity.

8. Standard sterile screw-capped culture tubes.

9. Air bath incubator, 35° C.

METHOD

Three control tubes containing 5.0 milliliters of broth were prepared for each organism to be tested, a total of nine tubes. Each tube set of three was inoculated with approximately $10^6$ organisms per milliliter from a stock culture. The pH of the culture mediums was about 7. Additionally, two spectrophotometer blanks were prepared. MCC and DCC were added to one tube in each set to effect a copper level of 0.5 milligrams per milliliter. Schematically the protocol was as follows in Chart I:

CHART I

| Tube | Broth | S.A. | P.A. | A.A. | MCC | DCC |
|------|-------|------|------|------|------|------|
| SA 1 | 5ml | 0.05ml | — | — | 11.7mg | 0 |
| SA 2 | 5ml | 0.05ml | — | — | 0 | 7.1mg |
| SA 3 | 5ml | 0.05ml | — | — | 0 | 0 |
| PA 1 | 5ml | — | 0.07ml | — | 11.7mg | 0 |
| PA 2 | 5ml | — | 0.07ml | — | 0 | 7.1mg |
| PA 3 | 5ml | — | 0.07ml | — | 0 | 0 |
| AA 1 | 5ml | — | — | 0.09ml | 11.7mg | 0 |
| AA 2 | 5ml | — | — | 0.09ml | 0 | 7.1mg |
| AA 3 | 5ml | — | — | 0.09ml | 0 | 0 |
| Blank 1 | 5ml | 0 | 0 | 0 | 11.7mg | 0 |
| Blank 2 | 5ml | 0 | 0 | 0 | 0 | 7.1mg |

Following immediate quantitation and viability testing, all tubes were loosely capped and incubated for 48 hours at 35° C., after which the tests were repeated. Results are indicated on Chart II.

CHART II

RESULTS OF QUANTITATION AND VIABILITY TESTS

| | Immediate | | | | After 48 Hours | | | |
|------|------|------|------|------|------|------|------|------|
| Tube | Undiluted OD | #/ml | Culture | Plate Count | Undiluted OD | #/ml | Culture | Plate Count |
| SA 1 | .25 | $9.0 \times 10^5$ | Viable | $3.0 \times 10^5$ | .24 | $\sim 8.0 \times 10^5$ | Sterile | 0 |
| SA 2 | .25 | $9.0 \times 10^5$ | Viable | $8.0 \times 10^5$ | OS | $>3.0 \times 10^6$ | Viable | $400 \times 10^6$ |
| SA 3 | .25 | $9.0 \times 10^5$ | Viable | $8.0 \times 10^5$ | OS | $>3.0 \times 10^6$ | Viable | $500 \times 10^6$ |
| PA 1 | .35 | $1.3 \times 10^6$ | Viable | $3.0 \times 10^5$ | .36 | $\sim 1.3 \times 10^6$ | Sterile | 0 |
| PA 2 | .35 | $1.3 \times 10^6$ | Viable | $2.0 \times 10^6$ | OS | $>3.0 \times 10^6$ | Viable | $60 \times 10^6$ |
| PA 3 | .35 | $1.3 \times 10^6$ | Viable | $1.9 \times 10^6$ | OS | $>3.0 \times 10^6$ | Viable | $50 \times 10^6$ |
| AA 1 | .30 | $1.1 \times 10^6$ | Sterile | 0 | .30 | $\sim 1.1 \times 10^6$ | Sterile | 0 |
| AA 2 | .30 | $1.1 \times 10^6$ | Viable | $10^6$ | OS | $>3.0 \times 10^6$ | Viable | $400 \times 10^6$ |
| AA 3 | .30 | $1.1 \times 10^6$ | Viable | $10^6$ | OS | $>3.0 \times 10^6$ | Viable | $400 \times 10^6$ |
| Blank 1 | 0 | 0 | N/A | N/A | 0 | 0 | N/A | N/A |
| Blank 2 | 0 | 0 | N/A | N/A | 0 | 0 | N/A | N/A |

The above test results indicate clearly that MCC possesses marked biocidal activity in reference to all test organisms. Particularly notable is the decrease in viable organisms in the "immediate" phase about 5 minutes after addition of MCC. It is equally obvious that DCC exhibits little, if any, biocidal activity, although some marginal control of Staphylococcus aureus was noted after 48 hours of incubation.

Also, these tests demonstrate that MCC is completely soluble in aqueous solutions and hence was easily dissolved in the broth. On the other hand, DCC is insoluble in aqueous media, and forms a cloudy suspension which completely settles out in a few minutes. Therefore, prior to making OD (optical density) readings, the DCC-containing tubes were permitted to settle until a constant reading was obtained, indicating that measured turbidity was, in fact, due to the bacterial particles. The turbidity test, while fairly accurate quantitatively, gives no indication of actual viability of the organisms. Hence, it was necessary to utilize a bio-assay method for determining viability as well as to confirm actual counts of viable organisms.

In addition to the above, the antimicrobial activity of the dialkali monocopper (II) citrates has been established by their toxic and growth-inhibiting action against the following microbes in mediums of oil emulsions employed as coolants in various machining operations where the pH of the coolant baths and liquids were on the order of about 9 to about 10. Such production coolant compositions are described in U.S. Pat. No. 3,244,630 and "American Society of Tool Engineers—Tool Engineer's Handbook", first edition, 1953, pages 357 et sequal, and such disclosures are incorporated herein by reference.

Aerobacter aerogenes
Aspergillus niger
Bacteroides
Bacillus subtilis
Candida albicans
Citrobacter
Enterobacter cerratia
Enterobacter cloacae
Escherichia coli
Klebsiella-Aerobacter
Neisseria catarrhalis
Proteus (Providence Group)
Proteus mirabilis
Proteus morgani
Proteus rettgeri
Proteus vulgaris
Pseudomonas aeruginosa
Pseudomonas fluorescens
Salmonella species
Staphylococcus albus
Staphylococcus aureus
Staphylococcus epidermidis
Streptococcus fecalis
Streptococcus viridans The above efficacy of antimicrobial activity was established in industrial coolant liquids where the listed microbes were found to proliferate. It is significant that even at these high pH's which are necessary for coolant liquid performances, the dialkali monocopper (II) citrates were remarkably effective. It is to be appreciated, furthermore, for example, that approximately 100 times more free copper would be made available at pH 8.5 than at pH 9.5 with reference to the attached drawing of the dissociation curve. Similarly, as the pH decreases below 8.5, even significantly greater amounts of toxic copper ion are released. Such tests demonstrate the applicability of the antimicrobial agents of this invention. Furthermore, industrial coolant baths were monitored over periods of several months and it has been established that the antimicrobial agents of this invention are effective over considerable periods of weeks without diminution in activity attributable to the controlled release of copper ion upon demand in the coolant baths.

As mentioned above, the metal complexes can be employed in aqueous solution or in solid form. Antimicrobial activities can be achieved upon the addition of an effective amount of either form. Furthermore, it is not necessary to remove other by-product salts from the prepared complexes to achieve the activity. However, by-product water and salt as described in the above procedures may surprisingly be removed to form solid complexes or concentrates. This achieves several goals, e.g., removes a contaminant material which may be detrimental in the utilization of the complex in practical applications, giving rise to excessive salt concentrations or corrosion problems; and enables the preparation of more highly concentrated active ingredient solutions which would enable storage bulk reduction, a definite advantage in industrial applications thereby reducing shipping and storage costs. Also, for other antiseptic, sanitizer, germicidal, bactericidal, sporicidal, virucidal, or disinfectant uses, it may be desirable to have as pure a complex preparation as possible.

IV. METALWORKING ACTIVITY

Metalworking fluid compositions, as explained above, can be formulated from many different types of specific ingredients. See for example the patents mentioned above and "American Society of Tool Engineers—Tool Engineer's Handbook", First Edition, 1953, pp. 357 et sequal, and such disclosures are incorporated herein by reference.

Without limitation, therefore, the following specific examples are illustrative of metalworking fluids and demonstrate the principles of this invention.

EXAMPLE 1.

A cutting fluid composition is prepared by mixing the following ingredients on a volume basis.
1% Sodium xylene sulfonate
9% Naphthene sulfonate
90% Mineral oil, approximately 300 vis.

This mixture is then used to prepare a 3% (volume) emulsion by blending with water and the pH is adjusted to about 8.5–8.9 with the addition of HCl. The disodium mono cupric citrate as prepared above is added to the emulsion to provide 100 mg/liter of $Cu^{++}$ in the aqueous phase. When such a metalworking fluid is employed in metal cutting operations, it has been found that all the advantages hereto discussed can be achieved.

EXAMPLE 2.

A grinding fluid composition is provided employing the same steps as Example 1 with similar results, except 50% naphthene sulfonate, 15% mineral oil (approximately 100 vis.) and 35% tall oil were substituted for the emulsion ingredients.

For the purpose of demonstrating the coordination of metal ions with the emulsified droplets to achieve stabilizing activities according to this invention, the following experiments were performed.

EXPERIMENT 1. Relation of Copper Concentration in the Oil and Water Phases to Percent Oil in the Emulsion and to Initial Metal Complex Concentration.

METHODS

Emulsions were prepared, to contain 2.5, 5.0 and 10.0% oil in water. Ten ml of each emulsion were pipetted into 16×100 ml test tubes. One ml samples of each were removed. Disodium mono cupric citrate (hereinafter metal complex) was added to each of these tubes to attain final concentrations of 50, 100 and 150 ppM as $Cu^{++}$. One ml samples were removed immediately after the metal complex and emulsions were mixed. Samples were taken again after 1 hour with occasional mixing during that period.

The oil samples were extracted by adding an equal volume of dichloroethane and 1 drop of saturated KCl, mixing, and spinning for 5 minutes at top speed on the table-top centrifuge. Five-tenths ml of the organic (bottom) layer and 0.1 ml of the aqueous were removed to different test tubes, and 4.9 ml of water were added to the aqueous sample. Two-tenths ml of copper reagent #1 were added to each tube, with mixing and then 0.2 ml of reagent 190 2 were added. All tubes were mixed well and 5.0 ml of water were added to the tubes containing the organic extract. The tubes containing the organic phase were mixed again and the organic material was allowed to settle to the bottom. Optical densities of the tubes were read at 700 nm against the appropriate blanks (organic or aqueous extract of emulsions with no metal complex added).

RESULTS AND CONCLUSIONS

The experimental findings are tabulated below. The percent copper in each phase was determined by correcting the $A_{700}$ for volume differences between the organic and aqueous extracts and adding the $A_{700}$ values for each phase. The "percent total $A_{700}$" of each phase was assumed to be directly related to the percent of total copper in each phase:

TABLE 1:

Percent Total Copper in each Phase as a Function of Time (T), Percent Oil and Copper Concentration

| | 50 ppM Metal Complex as $Cu^{++}$ Percent Total $Cu^{++}$ | | | |
|---|---|---|---|---|
| | Organic Phase | | Aqueous Phase | |
| % Oil | $T_0$ | $T_{60}$ | $T_0$ | $T_{60}$ |
| 2.5 | 0.9 | 0.0 | 99.1 | 100.0 |
| 5.0 | 13.0 | 22.7 | 87.0 | 77.3 |
| 10.0 | 19.2 | 25.9 | 80.8 | 74.1 |
| | 100 ppM Metal Complex as $Cu^{++}$ Percent Total $Cu^{++}$ | | | |
| | Organic Phase | | Aqueous Phase | |
| % Oil | $T_0$ | $T_{60}$ | $T_0$ | $T_{60}$ |
| 2.5 | 0.8 | 3.6 | 99.2 | 96.4 |

TABLE 1:-continued

| Percent Total Copper in each Phase as a Function of Time (T), Percent Oil and Copper Concentration | | | | |
|---|---|---|---|---|
| 5.0 | 10.6 | 12.2 | 89.4 | 87.8 |
| 10.0 | 12.7 | 13.6 | 87.3 | 86.4 |

| 150 ppM Metal Complex as $Cu^{++}$ Percent Total $Cu^{++}$ | | | | |
|---|---|---|---|---|
| | Organic Phase | | Aqueous Phase | |
| % Oil | $T_0$ | $T_{60}$ | $T_0$ | $T_{60}$ |
| 2.5 | 1.0 | 1.0 | 99.0 | 99.0 |
| 5.0 | 8.4 | 11.7 | 91.6 | 88.3 |
| 10.0 | 11.9 | 12.6 | 88.1 | 87.4 |

The results showed clearly that at any one metal complex concentration the percent total copper in the organic phase increased slowly with time. This effect was most marked in the samples containing 5.0% oil in the emulsion. The adsorption of $Cu^{++}$ into the oil layer appears to be, in enzymologic terminology, first order with respect to concentration of both oil and metal complex, with the concentration of copper in the oil leveling off at the saturation point of the oil. A Michaelis-Menten curve is expected for rate of transfer of $Cu^{++}$ into the oil phase, as is discussed below.

At a given time and metal complex concentration, the percent total copper in the organic phase was directly related to the percent oil in the emulsion. The correlation was most obvious in the 50 ppM metal complex samples. The amount of copper in the organic phase was dependent on the concentration of oil in the sample, indicating that copper was binding or coordinating directly to the surface of the oil particles.

As the metal complex concentration was increased, an equivalent increase in percent $Cu^{++}$ in the organic phase was not seen. This phenomenon suggests several different mechanisms of $Cu^{++}$ transfer into the oil. The size of oil particles in the emulsion is certainly not uniform. Therefore, the total oil particle surface area in the 10.0% oil emulsion was not 4 times as great as that in the 2.5% oil emulsion. The variation in particle size affects the amount of copper that can be transferred into the organic layer. An equilibrium may exist between copper in the oil and water phases. The 'equilibrium constants' for transfer in both directions may be determined by concentrations of metal complex in the aqueous phase, i.e., the reactant concentration, and concentrations of organic copper and citrate salts. The transfer of metal complex can be described as follows:

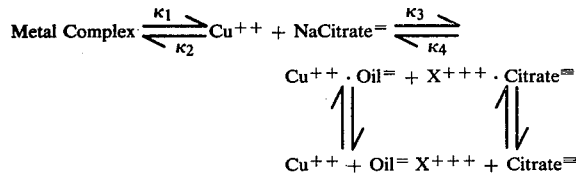

Where $X^{+++}$ is any simple or complex cation carrying 3 positive charges; $\kappa_1$ is determined by the dissociation constant of metal complex at pH 9, and $\kappa_3$ by the rate of adsorption of copper into the oil phase and the affinity of citrate and di- and tri-valent cations for each other. Evidently, $\kappa_1 > \kappa_2$ and $\kappa_3 < \kappa_4$, since with greatly increased time and shearing, virtually all copper has been found in the organic phase. The notions of an equilibrium relationship and time dependence for adsorption correlate well with Michaelis-Menten-like curves.

EXPERIMENT 2: Relation of Copper Concentration in the Oil and Water Phases to Shearing of Oil Particles.

METHODS.

A 50% oil concentrate was sheared by passing three times through a homogenizer at 8000 p.s.i. The oil particles were found to be under 0.1 μm in diameter. The same concentrate, unhomogenized, was found to have a wide range of oil particle size, 0.8–3 μm, with the average diameter approximately 1.5 μm.

The two concentrates were mixed with tap water to obtain 10% oil in water emulsions, since this percent oil emulsion was shown in the previous experiment to yield the greatest rate of adsorption of $Cu^{++}$ into the oil phase. A 2 ml sample of each emulsion was taken and centrifuged to remove any gross particulate matter. Metal complex was added to each emulsion to yield 100 ppM as $Cu^{++}$ and 2 ml samples were removed and centrifuged immediately. One ml aliquots of the supernatants were extracted and assayed as described in EXPERIMENT 1. The emulsions were shaken gently for 1 hour and 2 ml samples were removed and treated as described above after 10, 30 and 60 minutes.

RESULTS: The experimental findings are tabulated below. The percent copper in each phase was determined as described in EXPERIMENT 1.

TABLE 2:

| Percent Total Copper in each Phase as a Function of Time and Homogenization | | | | |
|---|---|---|---|---|
| | Percent Total $Cu^{++}$ (100 ppM Metal Complex Added) | | | |
| | Organic Phase | | Aqueous Phase | |
| Time (min.) | Homogenized | Unhomogenized | Homogenized | Unhomogenized |
| 0 | 13.5 | 11.3 | 86.5 | 88.7 |
| 10 | 18.3 | 20.3 | 81.7 | 79.7 |
| 30 | 25.3 | 14.9 | 74.7 | 85.1 |
| 60 | 27.0 | 18.1 | 73.0 | 81.9 |

A comparison of these results with those from EXPERIMENT 1 showed that considerably more copper had been adsorbed into the organic phase of the homogenized material and somewhat more into the organic phase of the unhomogenized material. If the concentration of metal complex added to these samples, particularly to the homogenized material, had been increased, a higher copper level in the organic layer would be expected. In a circulating metalworking coolant with high concentrations of divalent cations, such as $Mg^{++}$ and $Ca^{++}$, present to compete for the citrate moiety, the reaction rate for copper adsorption ($\kappa_1$ and $\kappa_3$) should be greater.

The results of this experiment demonstrate quite well the validity of a Michaelis-Menten analysis of the copper adsorption rate. The greatest rate of uptake of copper into the organic phase of the homogenized sample occurs in the first 10 minutes after metal complex had been added to the coolant. From 10 to 60 minutes a lower copper adsorption rate is noted. More copper has been taken up by the homogenized rather than unhomogenized oil particles. A far higher initial rate of copper adsorption is seen in the homogenized oil sample, due to the enormous surface area of the oil particles. These effects verify that copper adsorption to oil is also a surface phenomenon, i.e., that the copper binds to the surface of the oil particles rather than becoming incorporated into them.

In view of the above detailed description, it will be apparent that other modifications of these inventions may be made without departing from the spirit and scope thereof.

What is claimed is:

1. A method of transporting metal ions in a medium containing a moiety demanding said metal ions by introducing into said medium in an effective amount a metal complex of a metal ion and a polyfunctional organic ligand, said complex having an aqueous proton induced dissociation property represented by a sigmoidally-shaped curve on a cartesian coordinate plot of the negative log of the metal ion concentration versus the negative log of the hydrogen ion concentration, said dissociation property causing the controlled release of metal ions upon demand of said moiety.

2. The method of claim 1 wherein said complex is a metal complex of a heavy metal ion and a polyfunctional organic ligand in a ratio of 1:1 of the metal ion to the ligand, said ligand selected from the group consisting of an organic acid and a substituted organic acid.

3. The method of claim 1 wherein said medium is controlled within a pH range on the order of about 3 to about 12.

4. The method of claim 3 wherein said pH is controlled within the range of about 4 to about 9.

5. The method of claim 2 wherein said pH is alkaline.

6. The method of claim 5 wherein said pH is alkaline within the range of about 9 to about 12.

7. The method of claim 1 wherein said complex is a dialkalimetal monoheavymetal chelate of an alpha-hydroxy polycarboxylic acid.

8. The method of claim 7 wherein said chelate is dialkalimetal monocopper(II) citrate.

9. The method of claim 8 wherein said chelate is in aqueous admixture.

10. The method of claim 8 wherein said chelate is a solid.

11. The method of claim 2 wherein the metal complex is a dialkalimetal monocopper(II) citrate complex.

12. The method of claim 11 wherein the medium has an alkaline pH.

13. The method of claim 11 wherein the pH range of the medium is from about 7 to about 9 and about 10% to about 0.1% of said copper ion in said complex is released within said range.

14. The method of claim 2 wherein said metal ion is selected from the group consisting of zinc, nickel, chromium, bismuth, mercury, silver, copper, and cobalt.

15. The method of claim 14 wherein said substituted organic acid is selected from the group consisting of hydroxy polycarboxylic, amino polycarboxylic, sulfhydro polycarboxylic, and phosphinol polycarboxylic.

* * * * *

UNITED STATES PATENT AND TRADEMARK OFFICE
CERTIFICATE OF CORRECTION

PATENT NO. : 4,180,473
DATED : December 25, 1979
INVENTOR(S) : Gerald L. Maurer et al It is certified that error appears in the above-identified patent and that said Letters Patent are hereby corrected as shown below:

Col. 2, line 43 "8" should be --9--

Col. 14, line 36 "reagent 190 2 were" should be --reagent #2 were--

Signed and Sealed this

Tenth Day of June 1980

[SEAL]

Attest:

SIDNEY A. DIAMOND

Attesting Officer     Commissioner of Patents and Trademarks